United States Patent [19]

Exner

[11] Patent Number: 5,506,883
[45] Date of Patent: Apr. 9, 1996

[54] MOBILE X-RAY APPARATUS

[75] Inventor: Wolfgang Exner, Dresden, Germany

[73] Assignee: Siemens Aktiengesellschaft, Munich, Germany

[21] Appl. No.: 216,314

[22] Filed: Mar. 23, 1994

[30] Foreign Application Priority Data

May 27, 1993 [DE] Germany ............... 43 17 713.1

[51] Int. Cl.⁶ .................................. H05G 1/02
[52] U.S. Cl. ............................ 378/198; 378/197
[58] Field of Search ...................... 378/197, 198, 378/210

[56] References Cited

U.S. PATENT DOCUMENTS

| | | | |
|---|---|---|---|
| 1,775,853 | 9/1930 | Goldfield | 378/197 |
| 3,801,790 | 4/1974 | Götzl et al. | 378/198 |
| 5,067,145 | 11/1991 | Siczek et al. | 378/198 |
| 5,332,181 | 7/1994 | Schweizer et al. | 248/123.1 |

FOREIGN PATENT DOCUMENTS

| | | |
|---|---|---|
| 0231969 | 8/1987 | European Pat. Off. . |
| 0293228 | 11/1988 | European Pat. Off. . |
| 7525125 | 2/1977 | Germany . |
| 8521246 | 4/1986 | Germany . |
| 8709994 | 10/1987 | Germany . |

OTHER PUBLICATIONS

"Ein neuer fahrbarer Röntgengenerator für den Einsatz in der Intensivstation; erste klinische Erfahrungen mit dem Mobilett," Lutz et al., Electromedica, vol. 4 (1982), pp. 116–119.

Primary Examiner—David P. Porta
Assistant Examiner—David Vernon Bruce
Attorney, Agent, or Firm—Hill, Steadman & Simpson

[57] ABSTRACT

A mobile x-ray apparatus has a support stand for an x-ray radiator which is mounted together with a control panel to form a unit. This unit is connected to a wheeled carriage so as to be pivotable around a vertical axis as a unit. This results in approximately the same weight distribution being present regardless of the angle at which the x-ray radiator is pivoted with respect to the supporting stand.

2 Claims, 2 Drawing Sheets

MOBILE X-RAY APPARATUS

BACKGROUND OF THE INVENTION

1. Field of the Invention

The present invention is directed to a mobile x-ray apparatus of the type having a control panel and a stand which supports an x-ray radiator, the control panel and the support stand being mounted on a wheeled carriage.

2. Description of the Prior Art

Mobile x-ray systems of the above-described general type are known wherein the x-ray radiator is carried at the end of a pivot arm, the opposite end of which is connected to the support stand. In such known systems, the support stand is mounted to the carriage on a vertical axis which extends through the support stand, so that the overall x-ray apparatus can be positioned and maneuvered. The support stand is itself rotatably mounted to the carriage so as to be rotatable around the aforementioned vertical axis. A mobile x-ray apparatus of this type is disclosed in German OS 2 212 510, corresponding to U.S. Pat. No. 5,067,145.

This known structure exhibits the problem of tilting as the angle which the pivot arm carrying the x-ray radiator makes with the vertical support stand increases, thereby displacing the center of gravity of the overall apparatus toward one of the outer edges of the carriage. If the pivot arm is to be placed at such a relatively large angle, additional stabilizing members ("footers") may be required at the carriage.

SUMMARY OF THE INVENTION

It is an object of the present invention to provide an x-ray apparatus of the type initially generally described which exhibits approximately the same weight distributions (i.e., the center of gravity does not significantly change position) regardless of the pivot angle of the x-ray radiator.

The above object is achieved in accordance with the principles of the present invention in an x-ray apparatus wherein the vertical support stand for the pivot arm which carries the x-ray radiator is formed together with the control panel as a unit, and this unit is mounted to a carriage so as to be rotatable as a unit around a vertical axis.

The advantage achieved by the structure of the x-ray apparatus in accordance with the principles of the present invention is that the control panel, which has a number of components arranged therein, acts as a counterweight for the x-ray radiator, by virtue of the control panel and the vertical support stand being mounted together as a unit. The control panel does not function as a counterweight in known systems, such as the apparatus disclosed in U.S. Pat. No. 5,067,145, because in those systems the axis around which rotation takes place extends through the support stand, and it is only the support stand, or the x-ray radiator at the end of the pivot arm, which is rotatable around the vertical axis relative to the carriage. The structure of the x-ray apparatus in accordance with the principles of the present invention permits the carriage to be moved parallel to a bed on which a patient to be examined is lying. Placement of a portion of the bed, which must be done in known systems in order to achieve the desired stability, is not needed when using the mobile x-ray apparatus in accordance with the invention.

DESCRIPTION OF THE PREFERRED EMBODIMENTS

Figure 1:
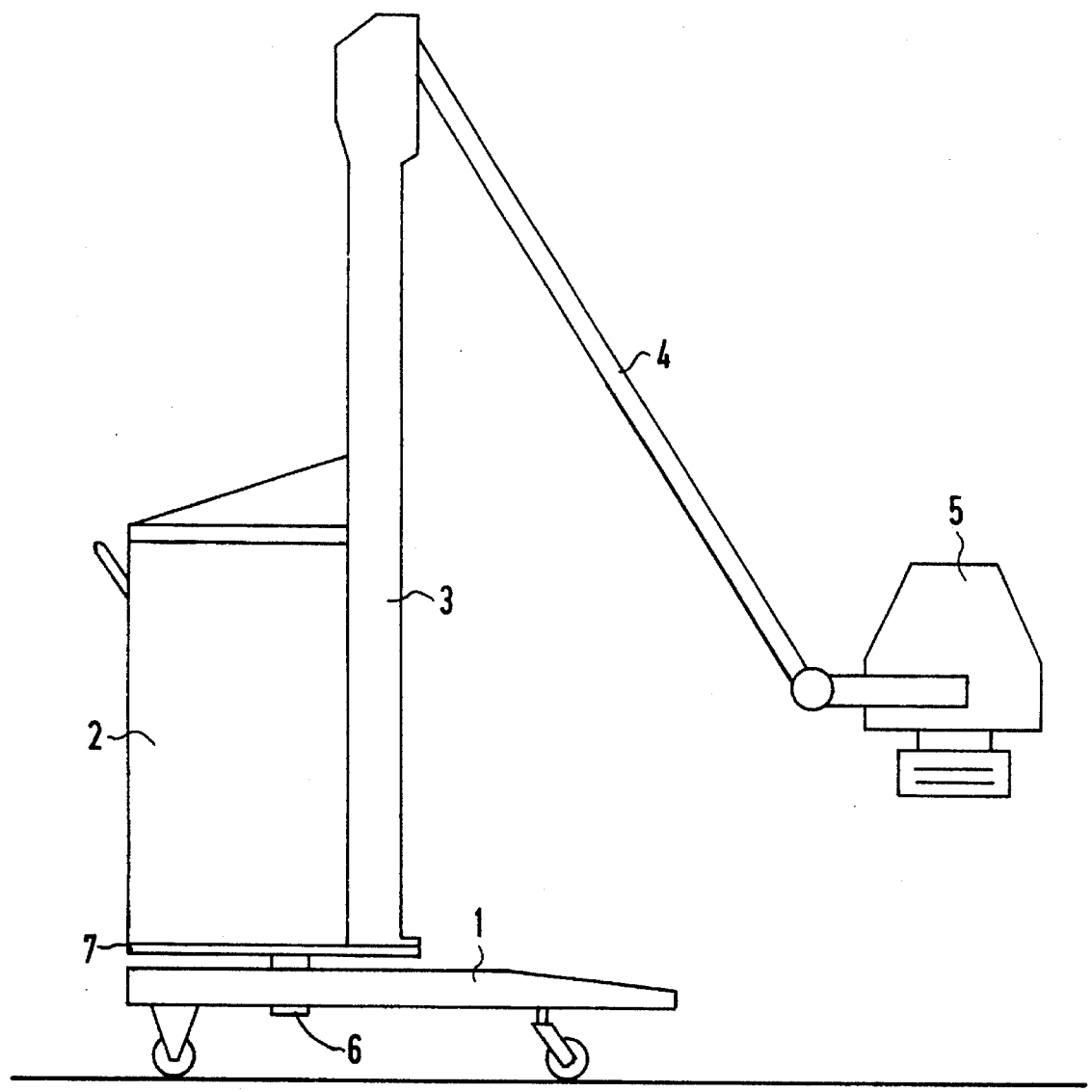
FIG. 1 is a side elevational view of a mobile x-ray apparatus constructed in accordance with the principles of the present invention.

The mobile x-ray apparatus shown in FIG. 1 includes a wheeled carriage 1 which is movable on the floor and which carries a control panel 2 and a support stand 3. An x-ray radiator 5 is connected to the support stand 3 via a pivot arm 4.

The control panel 2 and the support stand 3 are mounted together as a unit on an assembly base plate 7. The base plate 7 is connected to the carriage 1 so as to be rotatable around a vertical axis 6.

The control panel 2 and the support stand 3 are thus also rotatable around the vertical axis 6 as a unit.

Figure 2:
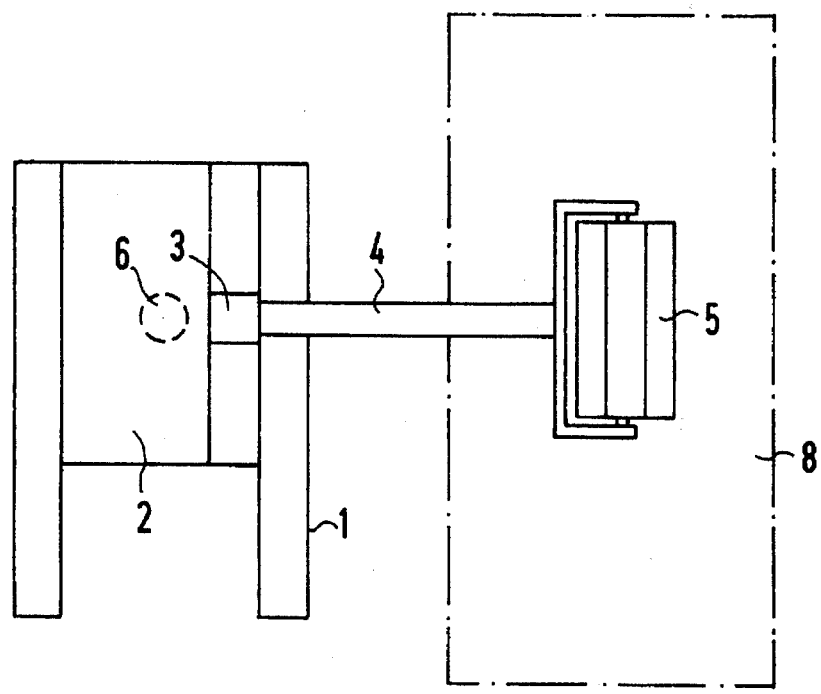
FIG. 2 is a plan view showing the mobile x-ray apparatus of FIG. 1 with the x-ray radiator extended over a patient's bed.

FIG. 2 shows the x-ray apparatus of FIG. 1 in the working position. In this position, the carriage 1 is aligned parallel to a bed 8, on which a patient to be examined is lying, and the x-ray radiator 5 is pivoted by 90° around the axis 6 compared to the position shown in FIG. 1, so that it is disposed over the patient on the bed 8. Moving the carriage 1 beneath the bed 8 is not necessary, because the control panel 2 operates as a counterweight to the x-ray radiator 5, due to the combined mounting of the stand 3 and the control panel 2 as a unit and due to the placement of the vertical axis 6 beneath that unit.

Figure 3:
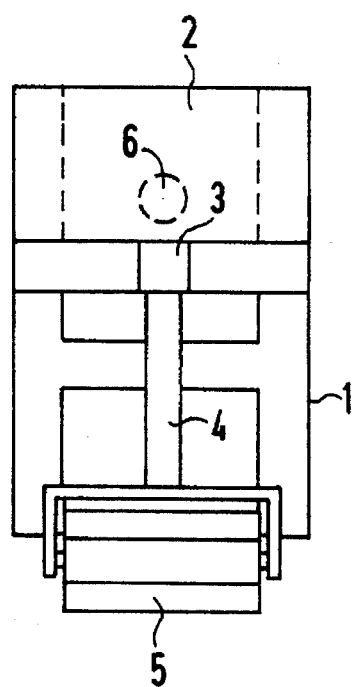
FIG. 3 is a plan view of the mobile x-ray apparatus of FIG. 1 with the components in a retracted position.

FIG. 3 shows all components of the mobile x-ray apparatus in a retracted position, wherein the pivot arm 4 carrying the x-ray radiator 5 is moved to its smallest angle relative to the support stand 3, so that the x-ray radiator 5 is at its lower-most position, closest to the carriage 1.

Although modifications and changes may be suggested by those skilled in the art, it is the intention of the inventor to embody within the patent warranted hereon all changes and modifications as reasonably and properly come within the scope of his contribution to the art.

I claim as my invention:

1. A mobile x-ray apparatus comprising:

an x-ray radiator;

a vertical support stand having a vertical support stand axis;

a pivot arm connecting said x-ray radiator to said support stand, said pivot arm being movable relative to said support stand to form an angle with said vertical support stand axis to selectively position said x-ray radiator;

a control panel secured to said support stand and forming a unit with said support stand;

a carriage movable along a floor; and means for mounting said unit formed by said support stand and said control panel for rotation relative to said carriage around a vertical rotational axis extending through said carriage and which is offset laterally from said support stand axis.

2. An x-ray apparatus as claimed in claim 1 wherein said means for mounting comprises an assembly base plate to which said control panel and said support stand are secured forming said unit, and a vertically oriented axle rotatably connecting said base plate to said carriage said vertical oriented axle containing said vertical rotational axis.

* * * * *